(12) United States Patent
Reich

(10) Patent No.: US 6,481,292 B1
(45) Date of Patent: Nov. 19, 2002

(54) DUAL PRESSURE MONITOR

(75) Inventor: Sanford Reich, Providence, RI (US)

(73) Assignee: Apex Medical, Inc., East Walpole, MA (US)

( * ) Notice: Subject to any disclaimer, the term of this patent is extended or adjusted under 35 U.S.C. 154(b) by 0 days.

(21) Appl. No.: 09/472,708

(22) Filed: Dec. 24, 1999

(51) Int. Cl.$^7$ .............................. G01L 7/02; G01L 1/22
(52) U.S. Cl. ..................... 73/730; 73/862.474
(58) Field of Search ................. 73/730, 753, 756, 73/714, 715–727, 862.474; 128/912; 604/27, 8–10, 164.01, 164.09, 164.11

(56) References Cited

U.S. PATENT DOCUMENTS

| | | | |
|---|---|---|---|
| 4,218,926 A | | 8/1980 | DeVisser |
| 4,250,876 A | * | 2/1981 | Kranz .................... 128/202.22 |
| 4,445,385 A | * | 5/1984 | Endo ........................... 73/726 |
| 4,676,255 A | * | 6/1987 | Cosman ...................... 600/561 |
| 4,796,641 A | * | 1/1989 | Mills et al. ................. 128/903 |
| 4,840,068 A | | 6/1989 | Mayhew, Jr. |
| 4,846,191 A | * | 7/1989 | Brockway et al. .......... 128/903 |
| 4,885,002 A | * | 12/1989 | Watanabe et al. ............. 73/753 |
| 5,410,916 A | | 5/1995 | Cook |
| 5,505,092 A | | 4/1996 | Kowalski |
| 5,564,434 A | | 10/1996 | Halperin et al. |
| 5,924,975 A | | 7/1999 | Goldowsky |
| 6,024,704 A | | 2/2000 | Meador et al. ............. 600/486 |

OTHER PUBLICATIONS

Guyton et al, Textbook of Medical Physiologies, W.B. Saunders Co., 1996, pp. 188–189 (No month).

Shiley Infusaid Inc., "Infuse–A–Port" product literature, 1987, 6 pages No month.

* cited by examiner

*Primary Examiner*—Harshad Patel
(74) *Attorney, Agent, or Firm*—Francis L. Conte

(57) ABSTRACT

A remote pressure sensor includes a probe having a chamber for holding a liquid. A flexible membrane is mounted in the probe. A conduit joins a reference cell to the chamber for holding the liquid. And, a reference pressure gauge is operatively joined to the conduit for measuring pressure of the liquid therein for use in referencing a primary pressure sensor through which fluid flows.

20 Claims, 2 Drawing Sheets

DUAL PRESSURE MONITOR

This invention was made with United States Government support under Cooperative Agreement No. 70NANB7H3059 awarded by NIST. The United States Government has certain rights in the invention.

BACKGROUND OF THE INVENTION

The present invention relates generally to pressure sensors, and, more specifically, to implantable pressure sensors.

In the medical field pertaining to living patients, pressure sensing of bodily fluids introduces the additional requirement of patient safety. For example, the measurement of blood pressure must not damage the blood itself or form clots therein which are detrimental to patient health.

Artificial heart pumps are being developed in the exemplary form of a Left Ventricular Assist Device (LVAD) which assists damaged hearts. Typical artificial heart pumps are configured for varying blood flowrate, frequency, and pressure as required to meet the typical demands placed on the heart which change in response to work effort. It is therefore desirable to control the heart pump by sensing blood pressure in the body.

In clinical practice, the tricuspid valve between the right atrium and right ventricle is chosen as the reference level for pressure measurement because this is one point in the circulatory system at which hydrostatic pressure factors caused by body position of a normal person usually do not affect the pressure measurement by more than 1 or 2 mm Hg. The reason for the lack of hydrostatic effects at the tricuspid valve is that the heart automatically prevents significant changes at this point by acting as a feedback regulator of pressure at this point.

For example, if the pressure at the tricuspid valve rises sightly above normal, the right ventricle fills to a greater extent than usual, causing the ventricle to pump more blood more rapidly and therefore to decrease the pressure at the tricuspid valve toward zero mm Hg. Thus all clinical blood pressure measurements are gauge pressure measurements referenced to barometric pressure and independent of barometric pressure, and referenced to the tricuspid valve level.

Since the heart pump is preferably fully implanted inside a patient, blood pressure must be also measured inside the body for controlling the pump. However, since it is not practical to directly measure blood pressure at the tricuspid valve, a suitable alternate pressure source must be provided.

Accordingly, it is desired to provide an implantable pressure monitor for measuring blood pressure referenced to outside barometric pressure for controlling a heart pump.

BRIEF SUMMARY OF THE INVENTION

A remote pressure sensor includes a probe having a chamber for holding a liquid. A flexible membrane is mounted in the probe. A conduit joins a reference cell to the chamber for holding the liquid. And, a reference pressure gauge is operatively joined to the conduit for measuring pressure of the liquid therein for use in referencing a primary pressure sensor through which fluid flows.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
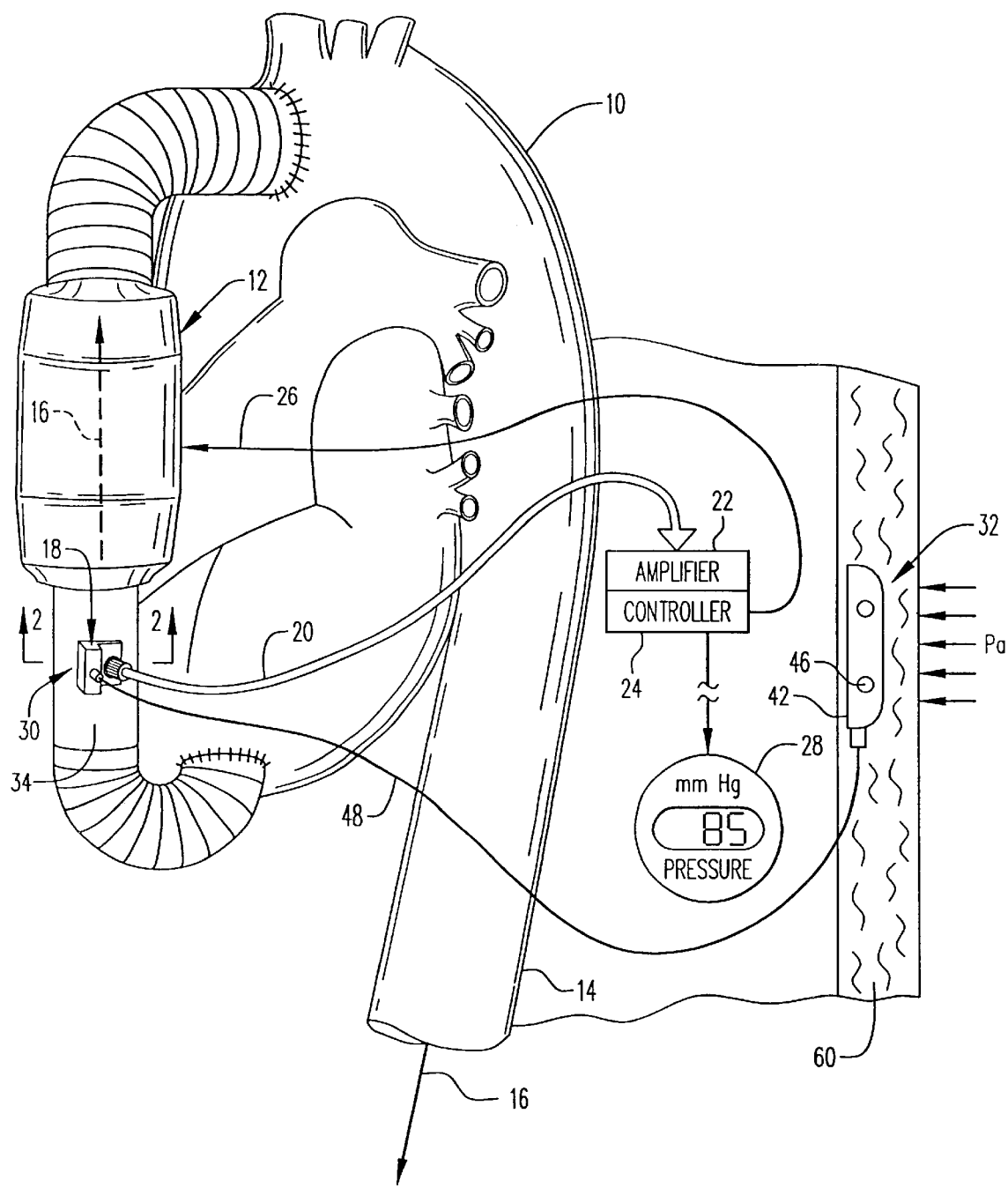
FIG. 1 is a schematic representation of a human heart inside the relevant portion of a human body, including a heart assist pump joined to the heart by an in vivo pressure monitor in accordance with an exemplary embodiment of the present invention.

Illustrated schematically in FIG. 1 is a human heart 10 inside the relevant portion of a living patient or body to which a Left Ventricular Assist Device (LVAD) or heart pump 12 is joined. The heart pump may take any conventional form and is sutured in the patient, in this case between the left ventricle of the heart and the main artery or aorta 14 for assisting in pumping fluid or blood 16.

In accordance with the present invention, a dual pressure monitor 18 joins the heart pump in flow communication with the left ventricle for carrying blood through the pump while simultaneously measuring pressure thereof. The pressure monitor is operatively joined by an electrical cable 20 to a conventional amplifier 22 which in turn is operatively joined to an electrical controller 24 which controls operation of the heart pump including its flowrate, frequency, and pumping pressure.

The controller 24 may take any conventional form, and is operatively joined also to the heart pump by another electrical cable 26 for controlling pumping of the blood though the pump in response to measured pressure from the pressure monitor. The controller is suitably configured for controlling blood flow though the pump into the aorta, and may optionally be joined to a suitable remote pressure indicator 28 for permitting external visual observation of the measured blood pressure which may be expressed in any suitable unit, such as millimeters of mercury (mm Hg).

Figure 2:
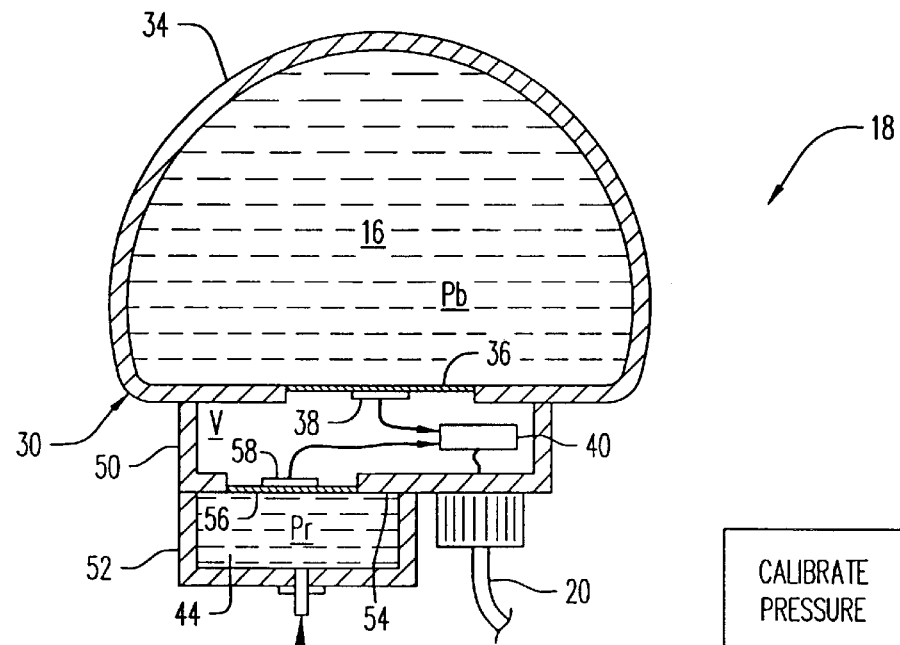
FIG. 2 is a partly sectional view of the pressure monitor illustrated in FIG. 1, including a primary pressure sensor joined to the heart pump and taken along line 2—2, and a cooperating remote pressure sensor implanted subcutaneously.
Figure 2:
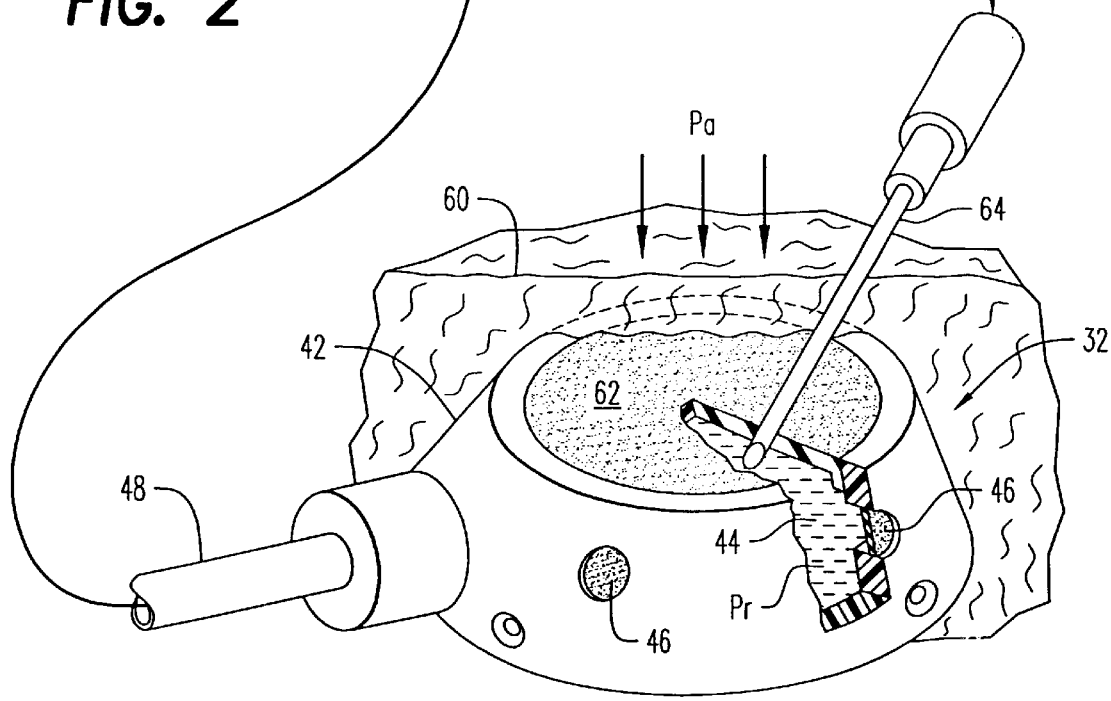

The pressure monitor 18 is illustrated in more particularity in FIG. 2 and is an assembly of a primary pressure sensor 30 and a remote or reference pressure sensor 32 cooperating therewith for measuring dual pressures for introducing a barometric or atmospheric pressure $P_a$ reference for the pressure $P_b$ of the blood 16.

The primary sensor 30 includes a cannula tube 34 through which the blood fluid 16 is channeled during operation of the pump. Since the fluid in this exemplary embodiment is blood, the tube is preferably formed of a hemo-compatible material, such as titanium, having proven benefits for carrying blood flow without incompatibility therewith. The tube is preferably smooth and seamless with a relatively thin wall.

The tube is primarily annular or cylindrical and includes a flat wall section having an opening in which is mounted a flexible primary diaphragm 36 which adjoins or bounds in part the fluid carried through the tube. The diaphragm is preferably planar and flat and may be made of thin titanium of about five mils (0.13 mm) thickness for being flexible under blood pressure.

Means in the exemplary form of a primary gauge 38 adjoin the diaphragm 36 on the outer surface thereof for measuring flexure of the diaphragm under pressure from the blood inside the tube. A suitable signal processor 40 is operatively joined to the primary gauge to determine the fluid pressure of the blood inside the tube as measured from flexure of the diaphragm caused by the fluid pressure.

In a preferred embodiment, the primary gauge 38 includes a plurality of conventional strain gauges mounted to the diaphragm for measuring strain therein due to flexure of the diaphragm under pressure. The strain gauges may take any conventional form and are typically adhesively bonded or joined by sputtering to the outer surface of the diaphragm in any suitable configuration, such as four in-line strain gauges.

The strain gauges are suitably electrically joined to the processor 40 for producing an electrical voltage signal as the diaphragm is elastically deformed under pressure. The pressure of the fluid inside the tube creates longitudinal and circumferential strain in the thin diaphragm as it flexes which is indicative of the pressure of the blood inside the tube 34. The signal processor is electrically joined to the amplifier 22 illustrated in FIG. 1 by the cable 20. The functions of the processor 40 and amplifier 22 may be separate or combined as desired, and located near the primary gauge 38 or at the pump controller 24 as desired.

Since blood pressure is being measured by induced strain in the diaphragm 36, that strain is based on the differential pressure acting across the diaphragm. Since the diaphragm is implanted in a living body, the nominal pressure therein is variable and unknown.

Accordingly, it is desired to provide a stable reference pressure inside the body for use in more accurately determining blood pressure. For in vivo conditions, a vacuum is considered to be a stable and practical reference since a vacuum may be maintained at a constant value, or vacuum pressure, and will not vary as temperature changes inside the body.

By providing a vacuum outside the diaphragm 36, the blood pressure measured by the primary gauge 38 is substantially an absolute pressure measurement which does not change as barometric pressure outside the body changes. However, as indicated above, clinical blood pressure measurements are preferably gauge pressure which are referenced to barometric pressure and are independent therefrom. Since barometric pressure changes due to weather high and low pressures and due to altitude above sea level, such changes are not reflected in the absolute pressure measured by the primary gauge 38.

In accordance with another feature of the present invention, a non-blood pressure inside the body must be discovered which is closely related to barometric pressure and independent of hydrostatic or other pressures in the body. Such a non-blood pressure must also be capable of measurement in vivo inside the body, yet must also be subject to calibration based on barometric pressure outside the body.

These objectives may be met by using the remote pressure sensor 32 illustrated in FIGS. 1 and 2. The remote sensor 32, illustrated in more detail in FIG. 2, includes a remote housing or probe 42 having an inside chamber for holding a liquid 44, such as saline water. One or more flexible reference membranes 46 are mounted in corresponding openings through the walls of the probe and adjoin or bound in part the inner chamber for transmitting external pressure on the membranes into the liquid contained in the chamber.

A conduit in the form of a catheter 48 is joined in flow communication with the probe chamber for defining a common reservoir therewith for the liquid to transmit the external pressure therethrough.

The remote probe 42 is operatively joined to the primary sensor 30 for providing a reference pressure thereto which is indicative of the barometric pressure outside the body. In the preferred embodiment illustrated in FIG. 2, a primary cell 50 is fixedly joined to the tube 34 outside the primary diaphragm 36 for providing an enclosed chamber therearound which may be suitably evacuated to a suitably low vacuum pressure V.

By introducing a vacuum in the primary cell 50, the pressure difference across the diaphragm 36 is increased and the measured pressure of the blood 16 is an absolute pressure relative to the degree of vacuum provided in the cell. Since the primary cell 50 is under vacuum, there is no opposing pressure on the diaphragm 36 which affects flexure of the diaphragm for more accurately determining the blood pressure inside the tube 34.

Furthermore, the vacuum inside the cell 50 does not change pressure therein due to changes in temperature at the primary cell as body temperature changes. Accordingly, the vacuum provides a stable reference pressure from which an accurate measurement of the blood pressure may be obtained by diaphragm flexure.

In order to reference the primary sensor 30 to atmospheric pressure, a secondary or reference cell 52 is fixedly joined to the primary cell 50 at a common wall 54 and is disposed in flow communication with the catheter conduit 48 for defining the common reservoir for holding the saline liquid 44 therein.

A flexible reference or secondary diaphragm 56 is mounted in an opening through the common wall 54 between the evacuated primary cell 50 and the saline filled secondary cell 52. The reference diaphragm 56 is thin and flat like the primary diaphragm 36 and may be similarly formed of thin titanium for similar operation.

Means in the exemplary form of a secondary or reference pressure gauge 58 adjoin the vacuum-side of the reference diaphragm 56 for measuring flexure thereof to determine pressure of the saline liquid 44 relative to the evacuated primary cell 50. In this way, the reference gauge 58 is operatively joined to the catheter conduit 48 and in turn to the remote probe 42 for measuring pressure of the liquid therein as transmitted through the non-compressible liquid from the pressure sensing membranes 46.

The reference gauge 58 may be identical to the primary gauge 38 and preferably includes a plurality of strain gauges mounted to the reference diaphragm 56 for measuring strain therein due to flexure thereof. The reference strain gauges 58 are similarly electrically joined to the signal processor 40 and in turn to the amplifier 22 and controller 24 illustrated in FIG. 1.

As shown in FIG. 1, the pressure monitor 18 is joined in flow communication with the heart pump 12 by the cannula 34 through which blood is pumped. The pump controller 24 is operatively joined to the primary and reference gauges 38,58 of the monitor through the cable 20. The controller 24 may thusly use the two pressures measured by the monitor for controlling flow the blood through the pump in response to blood pressure in the tube 34. Blood flowrate and pressure may be changed as desired in response to pressure measurement by the monitor 18.

The pressure monitor 18 may be used to advantage in controlling the heart pump 12 by implanting the heart pump 12 and tube 34 in series in the heart fully inside the patient without external exposure in the body. The remote probe 42 is preferably implanted subcutaneously below the skin 60 of the patient for being responsive to the barometric pressure exerted on the skin. The probe 42, catheter 48, and reference cell 52 as shown in FIG. 2 are completely filled with saline water to provide a continuous pressure conducting path from the sensing membranes 46 to the measuring reference diaphragm 56.

The pressure exerted on the skin is atmospheric pressure $P_a$, which is zero gauge pressure assuming that there is no tight clothing confining that particular skin location, or no object of significant weight exerting a force on that area of skin.

In general, pressure transmitted to subcutaneous tissue from its surroundings is the total tissue pressure(TTP). The TTP is the algebraic sum of the following two pressures:

(1) Interstitial fluid pressure (IFP): This pressure from the free fluid in the surrounding minute tissue spaces, as opposed to the surrounding interstitial fluid gel that normally constitutes 99% of the tissue fluid content. This pressure is independent of hydrostatic pressure because of the protein structure that creates the interstitial gel fluid structure. The IFP is normally negative (−) 2 mm Hg and typically ranges from −3 to −1 mm Hg when measured using a hypodermic needle inserted subcutaneously; and (2) Solid tissue pressure (STP): This pressure represents the force exerted by the solid elements of the tissues upon each other. These forces cause the cells and other solid structures to resist compression when negative pressure in the interstitial fluid sucks the solid structure against each other. It also causes much of the transmission of atmospheric pressure from the skin into the subcutaneous tissue.

When the probe 42 is implanted subcutaneously, an encased pocket of dense connective tissue will form therearound in approximately one month. The TTP may be slightly positive, but should be a relatively small and constant offset pressure relative to atmospheric pressure. The TTP value may go through some transition during the first month following implantation.

The anticipated constant offset pressure from subcutaneous implantation of the probe may increase by several mm Hg if a significant edema develops. When a significant edema occurs, the interstitial pressure may be as high as +6 mm Hg versus −2 mm Hg in the normal state.

A significant edema is said to be a pitting edema because one can press the thumb against the tissue area and push the fluid out of the area. When the thumb is removed, a pit left in the skin for a few seconds until the free fluid flow back from the surrounding tissues. A significant edema may result from many serious conditions including heart failure, kidney failure, bacterial infections, cancer, liver disease, and loss of plasma proteins from significant skin burns and wounds.

However, the TTP closely tracks barometric pressure in the normal physiological state and increases in value in disease or injury states that are easily detected by the presence of an edema. Under normal physiological states, the TTP pressure variations are expected to be within required accuracy of the primary pressure sensor 30, e.g., ±3 mm Hg.

Under abnormal physiological states, the TTP pressure variations are expected to shift to about three times the minimum expected primary sensor accuracy in the positive pressure side. This abnormal positive shift in barometric reference pressure will cause the gauge pressure to decrease by the same amount and be perceived as a decrease in primary pressure.

For example, if arterial pressure measured by the primary pressure sensor is decreased by 8 mm Hg, then the LVAD controller 24 may increase LVAD output to bring the arterial pressure back up by 8 mm Hg. Given the disease states that cause significant edema, the artifact in measuring barometric pressure represents a kind of feedback control system that may help to provide a small amount automatic compensation.

The primary pressure sensor 30 is attached to the probe 42 via the catheter 48 as shown in FIG. 2. The catheter material should preferably be of a higher durometer hardness with sufficient wall thickness in order to minimize internal volume changes caused by body movements, e.g., polyurethane. The saline filled catheter transmits the in vivo reference pressure $P_r$ within the probe to the outside surface of the reference diaphragm.

The advantage of locating the barometric reference strain gauge 58 within the primary pressure sensor 30 is to take advantage of the vacuum chamber 50, common regulated supply voltage, and common voltage/current feedthroughs for the supply voltage and ground.

Since the remote probe 42 illustrated in FIG. 2 is preferably implanted subcutaneously, it is not directly exposed to the ambient pressure $P_a$, and the reference pressure $P_r$ exerted inside the probe 42 may not be exactly equal to the barometric pressure. The reference pressure $P_r$ inside the probe is thusly a combination of the external barometric pressure $P_a$ and local internal pressures within the skin 60. The actual difference in the barometric pressure and the reference pressure may be determined during calibration, with a suitable offset factor being determined therefor.

Accordingly, the pressure monitor is preferably calibrated by comparing separately measured barometric pressure with the pressure measured by the remote probe, and determining any correction or offset factor which may be introduced into the pump controller 24 for improving accuracy. Since the probe is implanted below the skin 60, in vivo calibration is preferred which is minimally invasive to the patient.

For calibration purposes, the remote probe 42 illustrated in FIG. 2 further includes a resilient septum 62 mounted therein to define in part the liquid chamber thereof. In a preferred embodiment, the remote probe 42 and catheter 48 may be modified from a conventional injection port.

In a conventional injection port, the septum 62 is provided for repeatedly injecting fluid or drugs to a patient through the implanted port, with the catheter being routed to a desired vein or artery for delivering the fluid or drug thereto. The septum 62 is typically formed of silicone rubber and is relatively thick and rigid yet resilient. Hypodermic needles may be inserted through the skin and septum for delivering the fluid or drug into the port, with the puncture holes in the septum resiliently closing upon removal of the needle.

The remote probe 42 illustrated in FIG. 2 may be a relatively simple modification to a conventional injection port such as those sold under the INFUSE-A-PORT (trademark) brand by Shiley INFUSAID Inc., of Norwood, Mass. Such an injection port may be modified by the simple introduction of one or more of the thin resilient membranes 46 for transmitting external pressure into the saline liquid 44. By using multiple membranes 46 in the probe, common external pressures thereat will be applied to the liquid 44 and detected by the reference gauge 58. Since the septum 62 is relatively rigid, it is not effective for transmitting external pressure to the liquid 44 in view of the low pressures involved.

The reference membranes 46 illustrated in FIG. 2 are preferably slightly water permeable for automatically relaxing following transient changes in barometric pressure. Silicone rubber is a preferred choice for the reference membranes 46 since they permit slow water diffusion between the skin tissue and saline liquid 44 when the membranes are placed under external pressure.

This is particularly useful as barometric pressure changes due to weather, or due to elevation changes as a patient travels between sea level and the mountains. As the reference membranes are deflected or stressed under changes in barometric pressure, they will slowly relax to an unstressed state as water diffuses therethrough over one or more days. In this way, the reference probe 42 is self-nulling to changes in barometric pressure, which correspondingly ensures that the pressure monitor is referenced to the local barometric pressure.

External calibration of the pressure monitor is illustrated schematically in FIG. 2. A hypodermic or calibration needle 64 is inserted through the skin 60 and septum 62 of the remote probe. Additional saline water under a predetermined pressure may be injected through the needle 64 for pressurizing the saline liquid 44 in the probe to a suitable pressure, such as about 25 mm Hg above atmospheric pressure. The reference gauge 58 is then used for measuring strain in the reference diaphragm 56 to measure the pressure of the liquid in the referenced cell 52.

The calibration pressure applied inside the remote probe 42 may thusly be compared with the corresponding pressure measured by the referenced gauge 58 for suitable calibration. Calibration may be conducted at any individual point, such as at atmospheric pressure alone, or at a predetermined pressure above atmosphere, or both as desired for improving accuracy of use of the pressure monitor.

Calibration may be conducted externally by the simple injection of the hypodermic needle through the skin and septum. And, suitable precautions may be taken to ensure complete sterility of the calibration needle and any associated equipment cooperating therewith during the calibration procedure.

The dual pressure monitor disclosed above includes the primary pressure sensor for measuring substantially absolute pressure of the blood 16 in the cannula 34 and referencing this pressure to a substantially atmospheric pressure measured by the reference pressure sensor 32 all in a fully implantable device. In this way, the heart pump may be controlled based on gauge pressure of the blood, which is the difference of the measured atmospheric pressure from the remote probe 42 and the absolute pressure measured inside the cannula. The heart pump may thusly be more accurately controlled based on gauge pressure of the blood being pump, notwithstanding changes in atmospheric pressure external to the patient.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims in which I claim:

1. An in vivo implantable pressure monitor comprising:
   an implant probe having a chamber for holding a liquid,
   a flexible reference membrane mounted in an opening of a wall of said probe adjoining said chamber for transmitting external pressure to said liquid therein, and
   a resilient septum spaced from said reference membrane to define in part said chamber for receiving a hypodermic needle to calibrate said monitor; and
   a conduit joined in flow communication with said chamber for defining a common reservoir to hold said liquid for transmitting said external pressure therethrough.

2. A monitor according to claim 1 further comprising a reference pressure gauge operatively joined with said conduit for measuring pressure of said liquid therein.

3. A monitor according to claim 2 further comprising:
   a tube for channeling a fluid under pressure;
   a flexible primary diaphragm mounted in a wall opening of said tube to adjoin said fluid;
   a primary gauge adjoining said diaphragm for measuring flexure thereof to determine said fluid pressure;
   a processor operatively joined to said primary gauge to determine said fluid pressure from measured flexure of said diaphragm; and
   said reference pressure gauge being operatively joined to said processor for providing a reference pressure for said fluid pressure.

4. A monitor according to claim 3 further comprising:
   a primary cell joined to said tube outside said primary diaphragm, and being evacuated for increasing pressure difference across said diaphragm;
   a reference cell joined to said primary cell at a common wall, and disposed in flow communication with said conduit for defining said common reservoir to hold said liquid therein;
   a flexible reference diaphragm mounted in an opening of said common wall between said evacuated primary cell and said secondary cell; and
   said reference pressure gauge adjoining said reference diaphragm for measuring flexure thereof to determine pressure of said liquid relative to said evacuated primary cell.

5. A monitor according to claim 4 wherein said primary and reference gauges comprise strain gauges mounted to said primary and reference diaphragms for measuring strain therein under flexure thereof due to pressure thereacross.

6. A monitor according to claim 4 disposed in flow communication with a heart pump for pumping blood as said fluid, and further comprising a controller operatively joined to said primary and reference gauges and said pump, and configured for controlling flow of said blood through said pump in response to pressure of said blood through said tube.

7. A method of using said pressure monitor according to claim 6 comprising:
   implanting said heart pump and tube in series in a heart inside a living body for pumping blood therethrough;
   filling said probe, conduit, and reference cell with saline liquid; and
   implanting said probe subcutaneously in said living body for being responsive to barometric pressure.

8. A method according to claim 7 wherein said reference membrane is water permeable for relaxing following transient changes in barometric pressure.

9. A method according to claim 7 further comprising calibrating said pressure monitor by comparing barometric pressure with pressure measured by said probe.

10. A method according to claim 9 wherein said calibration further comprises:
    inserting a hypodermic needle through said septum of said probe
    pressurizing said liquid in said probe to a predetermined pressure; and
    measuring strain in said reference diaphragm to determine pressure of said liquid in said reference cell.

11. A monitor according to claim 1 wherein said probe wall laterally surrounds said chamber, said septum is disposed atop said probe for being implanted subcutaneously below skin, and said wall includes a plurality of said flexible reference membranes spaced laterally apart from each other for transmitting external skin pressure through said liquid in said chamber.

12. An in vivo implantable dual pressure monitor comprising:
   a primary pressure sensor including a tube for channeling a fluid, a flexible primary diaphragm mounted in a wall of said tube, and a primary gauge adjoining said diaphragm for measuring flexure thereof to determine pressure of said fluid; and
   a remote pressure sensor including an implant probe having a chamber for holding a liquid, a flexible reference membrane mounted in a wall of said probe, a reference cell adjoining said primary pressure sensor and including a reference diaphragm mounted in a wall of said cell, a conduit in flow communication between said reference cell and said probe to transmit pressure through said liquid, and a reference gauge adjoining said reference diaphragm for measuring flexure thereof to determine pressure of said liquid for referencing said fluid pressure.

13. A pressure monitor according to claim 12 further comprising:
   a primary cell joined to said tube outside said primary diaphragm, and being evacuated for increasing pressure difference across said diaphragm;
   said reference cell being joined to said primary cell at a common wall, and disposed in flow communication with said conduit for defining a common reservoir to hold said liquid therein;
   said reference diaphragm being mounted in an opening in said common wall between said evacuated primary cell and said reference cell; and
   said reference pressure gauge being mounted to said reference diaphragm for measuring flexure thereof to determine pressure of said liquid relative to said evacuated primary cell.

14. A monitor according to claim 13 wherein said primary and reference gauges comprise strain gauges mounted to said primary and reference diaphragms for measuring strain therein under flexure thereof due to pressure thereacross.

15. A monitor according to claim 14 disposed in flow communication with a heart pump for pumping blood as said fluid, and further comprising a controller operatively joined to said primary and reference gauges and said pump, and configured for controlling flow of said blood through said pump in response to pressure of said blood through said tube.

16. A method of using said pressure monitor according to claim 15 comprising:
   implanting said heart pump and tube in series in a heart inside a living body for pumping blood therethrough;
   filling said probe, conduit, and reference cell with saline liquid; and
   implanting said remote probe subcutaneously in said living body for being responsive to barometric pressure.

17. A method according to claim 16 wherein said reference membrane is water permeable for relaxing following transient changes in barometric pressure.

18. An in vivo implantable pressure monitor comprising:
   an implant probe having a chamber for holding a liquid;
   a flexible reference membrane mounted in a wall of said probe adjoining said chamber for transmitting external pressure to said liquid therein;
   a resilient septum spaced from said reference membrane to define in part said chamber for receiving a hypodermic needle to calibrate said monitor;
   a conduit joined in flow communication with said chamber for defining a common reservoir to hold said liquid for transmitting said external pressure therethrough;
   a reference cell joined in flow communication with said conduit for defining said common reservoir for holding said liquid;
   a flexible reference diaphragm mounted in an opening of a wall of said reference cell; and
   a reference gauge adjoining said reference diaphragm for measuring flexure thereof to determine pressure of said liquid in said reference cell.

19. A monitor according to claim 18 wherein said probe, conduit, and cell are filled with saline liquid, and said reference membrane is water permeable.

20. A monitor according to claim 18 wherein said probe wall laterally surrounds said chamber, said septum is disposed atop said probe for being implanted subcutaneously below skin, and said wall includes a plurality of said flexible reference membranes spaced laterally apart from each other for transmitting external skin pressure through said liquid in said chamber.

\* \* \* \* \*